US009031628B2

(12) United States Patent
Mao et al.

(10) Patent No.: US 9,031,628 B2
(45) Date of Patent: May 12, 2015

(54) DEVICE FOR ASSESSING ISCHEMIA IN NERVE ROOT TISSUE USING OXYGEN SATURATION

(75) Inventors: Jimmy Jian-min Mao, Fremont, CA (US); Robert E. Lash, Redwood City, CA (US); William Lyon, Sausalito, CA (US); Richard J. Fechter, San Rafael, CA (US)

(73) Assignees: ViOptix, Inc., Fremont, CA (US); Regents of the University of California, Oakland, CA (US)

( * ) Notice: Subject to any disclaimer, the term of this patent is extended or adjusted under 35 U.S.C. 154(b) by 1056 days.

(21) Appl. No.: 12/470,239

(22) Filed: May 21, 2009

(65) Prior Publication Data

US 2009/0292187 A1    Nov. 26, 2009

Related U.S. Application Data

(60) Provisional application No. 61/055,972, filed on May 24, 2008.

(51) Int. Cl.
*A61B 5/00*        (2006.01)
*A61B 5/1459*      (2006.01)
*A61B 5/145*       (2006.01)
*A61B 17/02*       (2006.01)

(52) U.S. Cl.
CPC ........... *A61B 5/1459* (2013.01); *A61B 5/14542* (2013.01); *A61B 17/025* (2013.01); *A61B 2017/0262* (2013.01)

(58) Field of Classification Search
USPC ......... 600/219, 323, 202, 210, 213, 218, 245, 600/201, 188, 199, 223; 606/207; 403/90
See application file for complete search history.

(56) References Cited

U.S. PATENT DOCUMENTS

| 3,394,700 | A |   | 7/1968  | Yamamoto      |         |
|-----------|---|---|---------|---------------|---------|
| 4,049,000 | A |   | 9/1977  | Williams      |         |
| 4,190,042 | A |   | 2/1980  | Sinnreich     |         |
| 4,226,228 | A |   | 10/1980 | Shin et al.   |         |
| D275,227  | S |   | 8/1984  | Garner, Jr.   |         |
| 4,597,382 | A |   | 7/1986  | Perez, Jr.    |         |
| 4,738,248 | A |   | 4/1988  | Ray           |         |
| 4,784,150 | A |   | 11/1988 | Voorhies et al. |       |
| 4,919,616 | A |   | 4/1990  | Croll         |         |
| 4,959,067 | A |   | 9/1990  | Muller        |         |
| D312,306  | S |   | 11/1990 | Michelson     |         |
| D318,116  | S |   | 7/1991  | Mlchelson     |         |
| 5,123,403 | A |   | 6/1992  | Lavyne        |         |
| 5,520,611 | A |   | 5/1996  | Rao et al.    |         |
| 5,529,571 | A | * | 6/1996  | Daniel        | 600/219 |
| 5,769,781 | A |   | 6/1998  | Chappuis      |         |
| 5,803,904 | A |   | 9/1998  | Mehdizadeh    |         |
| 5,817,005 | A | * | 10/1998 | Cohen         | 600/201 |

(Continued)

OTHER PUBLICATIONS

Nerve Root Retractors, Codman Surgical Product Catalog 380-385 (2004).

(Continued)

*Primary Examiner* — Brian Szmal
(74) *Attorney, Agent, or Firm* — Aka Chan LLP

(57) ABSTRACT

A retractor has an oximeter sensor at its tip, which allows measuring of oxygen saturation of a tissue being retracted by the retractor. The tip includes one or more openings for at least one source and detector. A specific implementation is a spinal nerve root retractor with an oximeter sensor.

27 Claims, 6 Drawing Sheets

(56) References Cited

U.S. PATENT DOCUMENTS

| | | |
|---|---|---|
| 5,891,018 A | 4/1999 | Wells |
| D411,883 S | 7/1999 | Farascioni et al. |
| D420,130 S | 2/2000 | Nicholas et al. |
| 6,078,833 A | 6/2000 | Hueber |
| D430,668 S | 9/2000 | Koros et al. |
| D433,134 S | 10/2000 | Pitesky |
| D442,687 S | 5/2001 | Schulz |
| D443,056 S | 5/2001 | Koros et al. |
| D453,377 S | 2/2002 | Schollhorn et al. |
| D457,957 S | 5/2002 | Sanford et al. |
| 6,416,465 B2 | 7/2002 | Brau |
| 6,516,209 B2 | 2/2003 | Cheng et al. |
| 6,587,701 B1 | 7/2003 | Stranc et al. |
| 6,587,703 B2 | 7/2003 | Cheng et al. |
| 6,597,931 B1 | 7/2003 | Cheng et al. |
| 6,735,458 B2 | 5/2004 | Cheng et al. |
| 6,801,648 B2 | 10/2004 | Cheng |
| 6,875,173 B2 | 4/2005 | Suddaby |
| D510,768 S | 10/2005 | Farley |
| 6,994,548 B2 | 2/2006 | Perret, Jr. |
| D533,946 S | 12/2006 | Lintner et al. |
| 7,226,413 B2 | 6/2007 | McKinley |
| 7,247,142 B1 | 7/2007 | Elmandjra et al. |
| 2008/0045822 A1* | 2/2008 | Phillips et al. ............. 600/323 |
| 2009/0259106 A1* | 10/2009 | Catapano et al. ............. 600/202 |

OTHER PUBLICATIONS

D.M. Hueber et al., "New Optical Probe Designs for Absolute (Self Calibrating) NIR Tissue Hemoglobin Measurements", Proc. SPIE 3597, pp. 618-631, Jan. 1999.

H. Taitelbaum et al., "Approximate theory of photon migration in a two-layer medium", Applied Optics, vol. 28, No. 12, pp. 2245-2249, Jun. 15, 1989.

S.J. Matcher et al., "Absolute qualification methods in tissue near infrared spectroscopy", Proc. SPIE vol. 2389, pp. 486-495, 1995.

D.T. Deply et al., "Quantification in tissue near-infrared spectroscopy", Phil. Trans. R. Soc. Lond. B352, pp. 649-659, 1997.

* cited by examiner

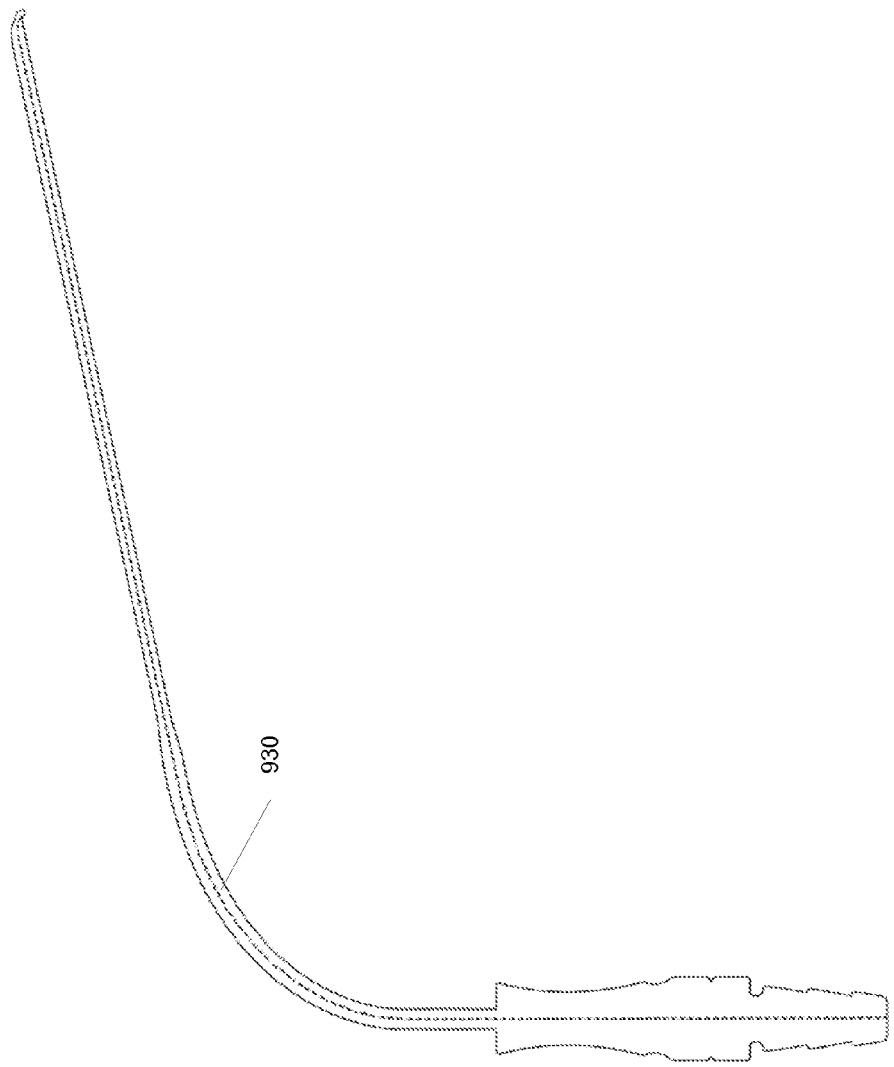

DEVICE FOR ASSESSING ISCHEMIA IN NERVE ROOT TISSUE USING OXYGEN SATURATION

CROSS-REFERENCE TO RELATED APPLICATIONS

This patent application claims the benefit of U.S. provisional patent application 61/055,972, filed May 24, 2008, which is incorporated by reference.

BACKGROUND OF THE INVENTION

This invention relates to the field of medical devices and more specifically to a retractor device with an oximeter sensor.

Retractors play an important role in medicine. Retractors typically retract or hold aside tissues so that a physician (e.g., surgeon) can gain access to an area for operation or observation. It is critical that the retracted tissue is not damaged.

One area of medicine that retractors are commonly used is during spinal surgery. Tens of thousands of spinal surgeries are performed each year. The number of spinal surgeries is continuing to increase due, in part, to an aging population, active lifestyles, and a better understanding of what causes back pain. Back pain may be due to disc herniation, degenerative disc disease, spinal trauma, and osteoarthritis just to name a few examples.

The spinal cord is the main pathway through which the brain sends and receives signals. The nerve fibers in the spinal cord branch off to form pairs of nerve roots that travel through small openings between the vertebrae. These nerves control the body's function including the vital organs, sensation, and movement.

During spinal surgery, it is often necessary to retract, or hold, the nerve root aside so that the surgeon can access the surgical site. With current medical devices, however, it is difficult if not impossible, to tell whether the nerve root is being damaged during the retraction. Damage to the nerve root can be catastrophic.

There is, then, a continuing demand for medical devices that provide patient feedback, provide more features, are easier to use, and generally address the needs of patients, doctors, and others in the medical community.

Therefore, there is a need to provide improved systems and techniques for nerve retractors.

BRIEF SUMMARY OF THE INVENTION

A retractor has an oximeter sensor at its tip, which allows measuring of oxygen saturation of a tissue being retracted by the retractor. The tip includes one or more openings for at least one source and detector. A specific implementation is a spinal nerve root retractor with an oximeter sensor.

The invention is a surgical nerve root retractor with tissue oxygen saturation sensing capability to potentially prevent nerve root hypoxia during spinal surgical retraction. This device will potentially be less expensive and easier to use than laser Doppler blood flow measurements and potentially more accurate in determining the effect of surgical manipulation on the health of nerve roots. This device will be easier to apply than conventional electrophysiological monitoring and is very precise in location.

In an implementation, the retractor has a steel shaft, a handle connected to a proximal end of the shaft, and a tip connected to a distal end of the shaft. The tip has a retractor portion or blade and an oximeter sensor. The blade is angled sufficiently with respect to a bottom surface of the tip to retract tissue, such as an angle of about 90 degrees. However, the angle may vary from about 90 degrees to about 179 degrees.

In an implementation, the retractor has an oximeter sensor including a first sensor opening and a second sensor opening on a bottom side of the tip. There is a first optical fiber and a second optical fiber. The first optical fiber passes through a channel in the shaft and a distal end of the first optical fiber is connected to a first sensor opening of the tip. The second optical fiber passes through the channel in the shaft and a distal end of the second optical fiber is connected to a second sensor opening of the tip. There is a display, connected to the oximeter sensor via optical fibers, to show an oxygen saturation measurement made by the oximeter sensor.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 9B shows an internal channel of a retractor.

DETAILED DESCRIPTION OF THE INVENTION

Figure 1:
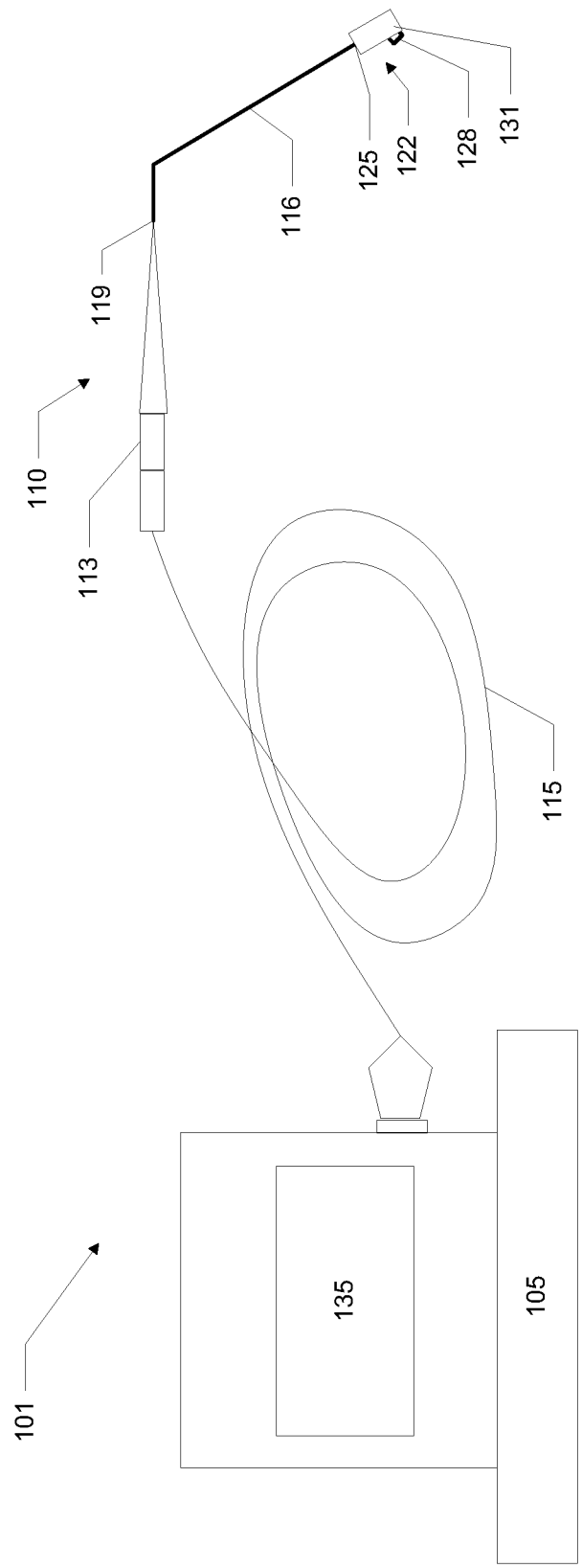
FIG. 1 shows an oximeter system for measuring oxygen saturation of tissue.

FIG. 1 shows an oximeter system 101 for measuring oxygen saturation of tissue, such as a nerve root. The system includes a monitoring console 105, a nerve root retractor 110, and a cable 115 connecting the nerve root retractor to the monitoring console. The cable includes optical fiber.

The nerve retractor has a handle 113, a shaft 116 connected at its proximal end 119 to the handle, and a tip 122 connected to a distal end 125 of the shaft. The tip includes a retractor portion or retractor blade 128 and an oximeter sensor 131.

The shaft includes an internal channel or passageway. Optical fibers pass from sensor openings on the tip, through the channel, through the handle, and into the cable jacket or cable insulation. See FIG. 9B, which shows a path of an internal channel (930) within a retractor. The shaft is made of steel.

The system is used by placing the oximeter sensor in contact with the nerve. Light is transmitted from the monitoring console, through optical fiber in the cable, out a sensor opening on the tip and into the nerve. The reflected light from the nerve is then received by another sensor opening on the tip, transmitted back to the monitoring console via optical fiber, and then processed. A screen 135 on the console displays the oxygen saturation measurement.

Figure 2:
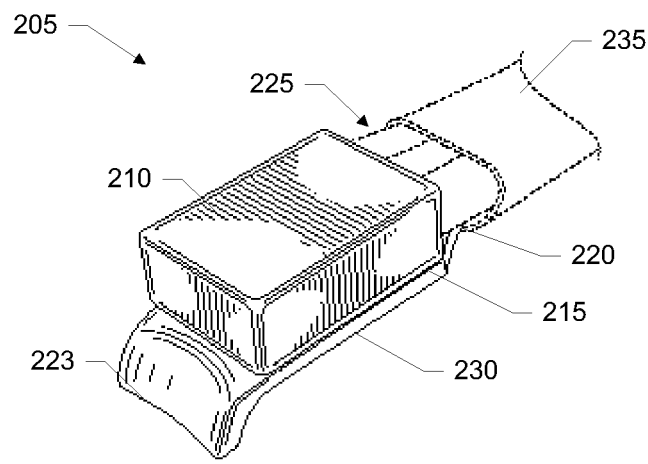
FIG. 2 shows a perspective view of a first implementation of a tip.

FIG. 2 shows a perspective view of a first implementation of a tip 205. The tip includes a retractor blade and an oximeter sensor 210 attached to a top surface 215 of the tip. The tip attaches to a shaft 220. The tip also includes a retractor portion 223. Optical fibers are encased in a cable jacket 225, travel along the shaft, into the oximeter sensor, and are exposed through an opening on a bottom surface 230 of the tip. Cable jacket 225 and shaft are wrapped with a tubing 235. Such tubing may be heat-shrink tubing.

In a specific implementation of FIG. 2, the tip of the retractor has a length of about 17.5 millimeters, width of about 8 millimeters, and a thickness (not including the retractor blade) of about 5 millimeters.

Figure 3:
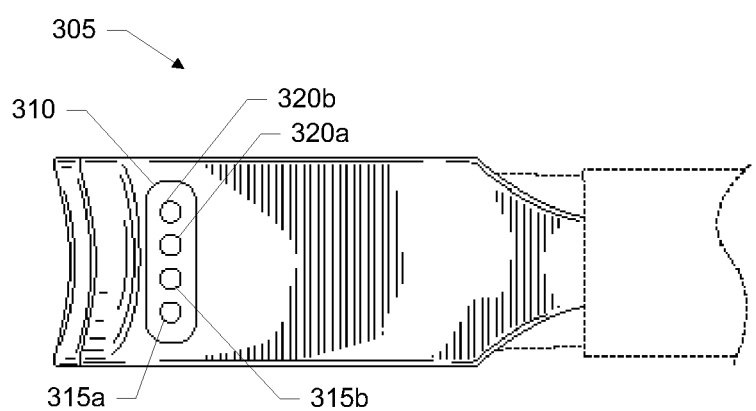
FIG. 3 shows a bottom view of the first implementation of a tip.

FIG. 3 shows a bottom view of the first implementation of a tip 305. The tip has a retractor blade and slot 310, within which there are sensor openings. There are four sensor openings for ends of fiber optic cables. The openings 315a, 315b, 320a, and 320b are for source and detector fibers.

Figure 4:
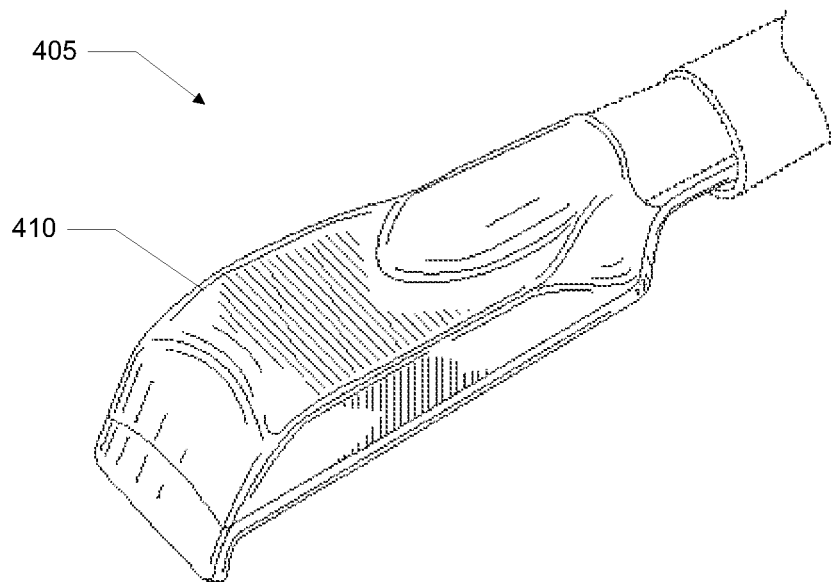
FIG. 4 shows a perspective view of a second implementation of a tip.

FIG. 4 shows a perspective view of a second implementation of a tip 405 with an encasement 410 which contains optical fiber attached to the tip.

In a specific implementation of FIG. 3, the tip of the retractor has a length of about 17.5 millimeters, width of about 8 millimeters, and a thickness (not including the retractor blade) of about 3 millimeters.

Figure 5:
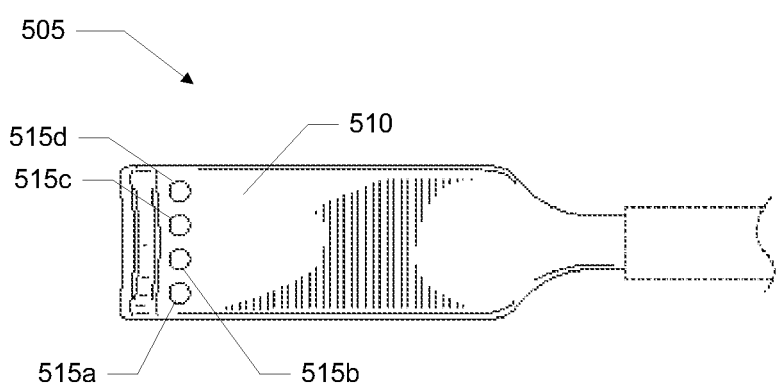
FIG. 5 shows a bottom view of the second implementation of a tip.

FIG. 5 shows a bottom view of the second implementation of a tip 505. The tip includes a retractor blade and four sensor openings on a bottom surface 510 of the tip. The sensor openings include openings 515a, 515b, 515c, and 515d. Optical fiber is connected to each of the sensor openings. The sensor openings can include sources and detectors.

Figure 6:
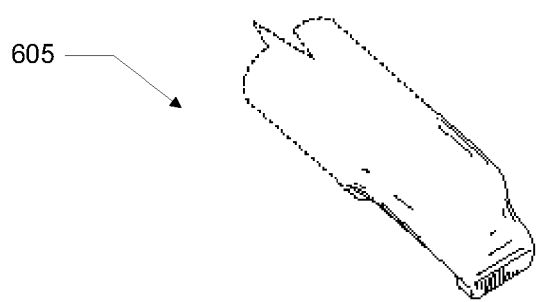
FIG. 6 shows a perspective view of a third implementation of a tip.
Figure 7:
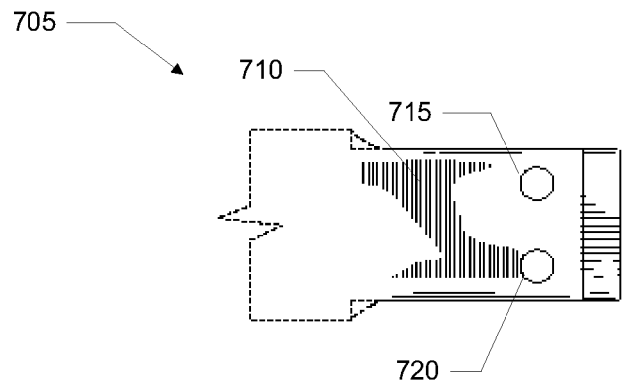
FIG. 7 shows a bottom view of the third implementation of a tip.

FIG. 6 shows a perspective view of a third implementation of a tip 605. FIG. 7 shows a bottom view of the third implementation of a tip 705. The tip includes two sensor openings on a bottom surface 710 of the tip. The two sensor openings include an opening 715 and an opening 720. The openings include a source and detector.

Figure 8:
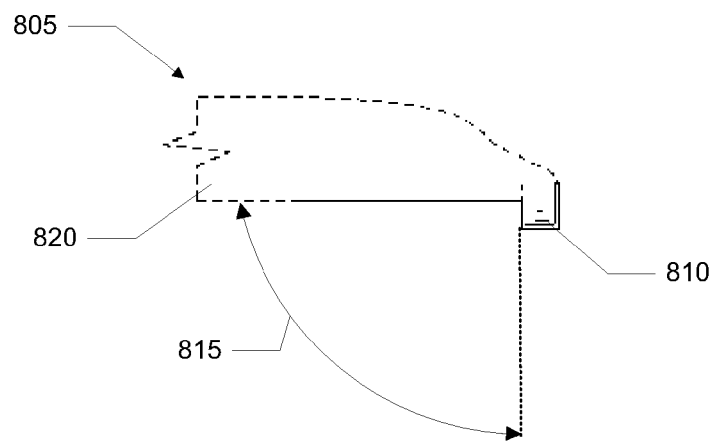
FIG. 8 shows a side view of the third implementation of a tip.

FIG. 8 shows a side view of the third implementation of a tip 805. A retractor portion or retractor blade 810 is at an angle 815 to a shaft 820 onto which the tip is attached. In an implementation, the angle is about 90 degrees. Angle 815 ranges from about 90 degrees to about 179 degrees.

In a specific implementation of FIG. 8, the tip of the retractor has a length of about 5 millimeters, width of about 3 millimeters, and a thickness (not including the retractor blade) of about 2 millimeters.

Figure 9A:
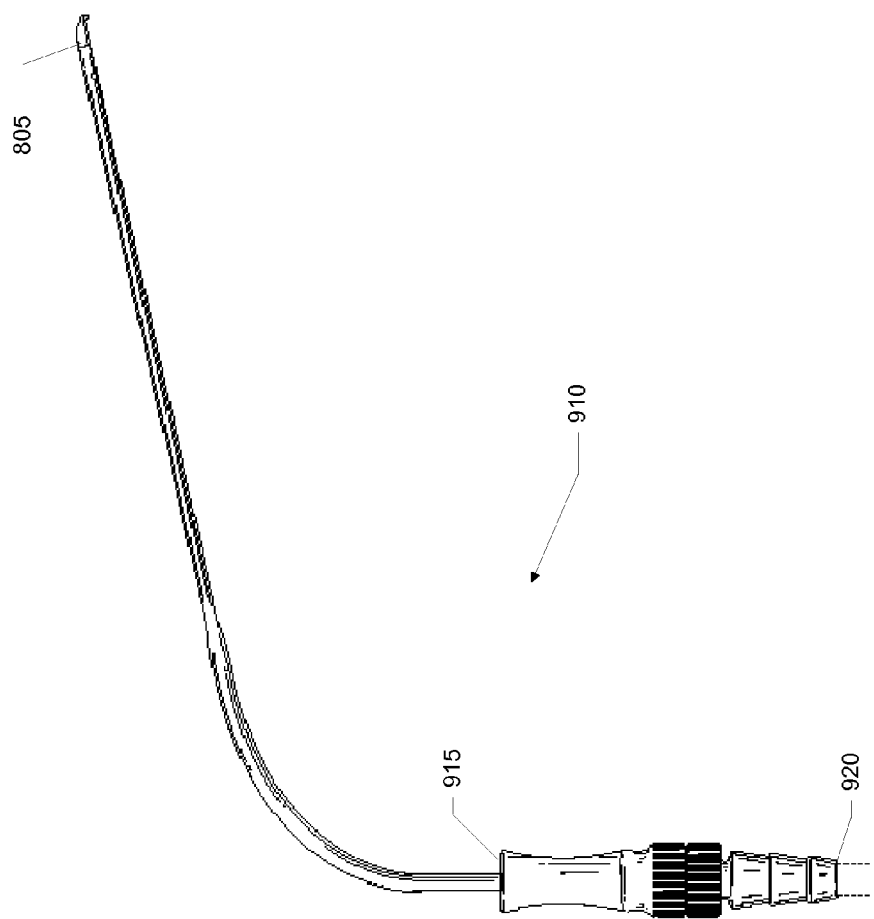
FIG. 9A shows a perspective view of the third implementation of the tip attached to a nerve retractor.

FIG. 9A shows a side view of the third implementation of the tip 805 connected to a nerve retractor 910. This figure shows the handle of the retractor, having a first end 915 and a second end 920, as shown. The handle connects to the shaft and the tip via the first end.

FIG. 9B shows a path of an internal channel 930 within a refractor.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A device comprising:
a shaft comprising a first portion of an internal channel that extends from a distal end to a proximal end of the shaft, wherein the shaft comprises a bend, positioned between the distal and proximal ends, that divides the shaft into first and second portions, and the first portion of the shaft is angled with respect to the second portion of the shaft;
a handle, coupled to the proximal end of the shaft, wherein the handle comprises a second portion of the internal channel extending from a first end to a second end of the handle, and the second portion of the internal channel couples to the first portion of the internal channel of the shaft;
a tip, coupled to the distal end of the shaft, wherein the tip comprises a third portion of the internal channel coupled to the first portion of the internal channel and the third portion of the internal channel extends through the tip to at least two oximeter sensor openings of the tip,
the tip comprises a planar surface comprising the at least two sensor openings and a retractor blade that is angled with respect to the planar surface at a blade-to-surface angle,
the refractor blade is angled with respect to the second portion of the shaft also at the blade-to-surface angle,
at a point where the first and third portions of the internal channel meet, the first portion of the internal channel of the shaft is aligned with the third portion of the internal channel of the tip without a change in direction, and
the at least two sensor openings are in a linear arrangement that is parallel to the retractor blade;
an enclosed passageway of the internal channel, extending contiguously from the sensor openings of the tip through the third portion of the internal channel, through the first portion of the internal channel of the shaft, and through the second portion of the internal channel to the second end of the handle; and
at least two optical fibers, coupled to the at least two sensor openings, wherein the at least two optical fibers extend through the enclosed passageway of the internal channel formed by the third, first, and second portions of the internal channel to the second end of the handle.

2. The device of claim 1 wherein the shaft comprises steel.

3. The device of claim 1 comprising:
an electronic display, coupled to the at least two optical fibers at a point after the fibers have passed through the handle and exited from the second end of the handle, to show an oxygen saturation measurement made using the oximeter sensor openings, wherein the handle is used as a grip for the device.

4. The device of claim 1 wherein on a side of the tip opposite of the planar surface with the at least two sensor openings, there are no sensor openings.

5. The device of claim 1 further comprising:
a first optical fiber of the at least two optical fibers; and
a second optical fiber of the at least two optical fibers,
wherein the first optical fiber is enclosed within the first portion of the internal channel in the shaft,
the second optical fiber is enclosed within the first portion of the internal channel in the shaft,
the first and second optical fibers are enclosed within the second portion of the internal channel from the first end of the handle to the second end of the handle, and
the first and second optical fibers exit the second end of the handle into a cable.

6. A system for measuring oxygen saturation comprising the device of claim 5, which is coupled to a monitoring console comprising a screen,
- whereby light is transmitted from the monitoring console, through the optical fibers in the cable, out a first sensor opening of the at least two sensor openings on the tip to a tissue,
- reflected light from the tissue is then received by a second sensor opening of the at least two sensor openings on the tip, transmitted back to the monitoring console via the optical fibers, and
- the monitoring console is configured to process the reflected light and to display the oxygen saturation measurement on the screen.

7. The device of claim 1 wherein four oximeter sensor openings are in a linear arrangement that is parallel to the retractor blade on the planar surface of the tip.

8. The device of claim 7 wherein at least one of the four oximeter sensor openings is a source and at least one of the four oximeter sensor openings is a detector.

9. The device of claim 1 wherein the shaft comprises only a single bend from the distal end to the proximal end.

10. The device of claim 1 wherein the shaft comprises a tube having a first diameter and the handle comprises a second diameter, greater than the first diameter.

11. The device of claim 1 wherein the handle comprises an elongated cylindrical member comprising a first opening at the first end, which is coupled to the shaft, and a second opening at the second end, and the second opening is opposite to the first opening.

12. The device of claim 11 wherein the second opening has a greater diameter than the first opening.

13. The device of claim 1 wherein the retractor blade is angled with respect to the planar surface at an angle greater than 90 degrees and less than 179 degrees.

14. The device of claim 1 wherein the retractor blade is angled with respect to the planar surface at an angle greater than or equal to 90 degrees and less than or equal to 179 degrees.

15. The device of claim 1 wherein the retractor blade is angled with respect to the second portion of the shaft at an angle greater than or equal to 90 degrees and less than or equal to 179 degrees.

16. The device of claim 1 wherein the retractor blade is angled with respect to the planar surface at an angle greater than 95 degrees and less than 175 degrees.

17. The device of claim 1 wherein the retractor blade is angled with respect to the second portion of the shaft at an angle greater than 90 degrees and less than 179 degrees.

18. The device of claim 1 wherein the retractor blade is angled with respect to the shaft at an angle greater than 95 degrees and less than 175 degrees.

19. The device of claim 1 wherein a width of the planar surface of the tip is less than a width of the shaft at the shaft's distal end.

20. A device comprising:
- a shaft comprising a first portion of an internal channel that extends from a distal end to a proximal end of the shaft;
- a handle, coupled to a proximal end of the shaft, wherein the handle comprises a second portion of the internal channel extending from a first end to a second end of the handle, and the second portion of the internal channel couples to the first portion of the internal channel of the shaft;
- a tip, coupled to a distal end of the shaft, wherein the tip comprises a third portion of the internal channel coupled to the first portion of the internal channel and the third portion of the internal channel extends through the tip to at least two oximeter sensor openings of the tip,
- the tip comprises a planar surface comprising the at least two sensor openings and a retractor blade that is angled with respect to the planar surface,
- at a point where the first and third portions of the internal channel meet, the first portion of the internal channel of the shaft is contiguous with the third portion of the internal channel of the tip without a change in direction, and
- the at least two sensor openings are in a linear arrangement that is parallel to the retractor blade; and
- at least two optical fibers, coupled to the at least two sensor openings, wherein the at least two optical fibers are placed in the first, second, and third portions of the internal channel,
- a path from the first opening of the handle to the second opening of the handle is linear, and
- a perimeter of the handle is greater than a perimeter of the shaft.

21. The device of claim 20 wherein the at least two oximeter sensor openings of the tip comprises:
- four oximeter sensor openings in a linear arrangement that is parallel to the retractor blade on the planar surface of the tip.

22. The device of claim 20 wherein the shaft comprises a bend, positioned between the distal and proximal ends of the shaft, such that a first portion of the shaft is angled with respect to a second portion of the shaft.

23. The device of claim 22 wherein the bend is the only bend between the distal and proximal ends of the shaft.

24. A device comprising:
- a shaft comprising a first portion of an internal channel that extends from a distal end to a proximal end of the shaft, wherein the shaft comprises a bend positioned between the distal end and the proximal end that divides the shaft into first and second portions;
- a handle, coupled to a proximal end of the shaft, wherein the handle comprises a second portion of the internal channel extending from a first end to a second end of the handle, and the second portion of the internal channel couples to the first portion of the internal channel of the shaft;
- a tip, coupled to a distal end of the shaft, wherein the tip comprises a third portion of the internal channel coupled to the first portion of the internal channel and the third portion of the internal channel extends through the tip to four oximeter sensor openings of the tip,
- the tip comprises a planar surface comprising the four sensor openings and a retractor blade is angled with respect to the planar surface,
- the refractor blade is angled with respect to a first axis of the first internal channel passing through the second portion of the shaft, and
- at least two of the four sensor openings are in a linear arrangement that is transverse to the first axis; and
- four optical fibers, coupled to the four sensor openings, wherein the four optical fibers are placed in the first, second, and third portions of the internal channel,
- wherein the handle comprises an elongated member comprising a first opening at the first end, which is coupled to the shaft, and a second opening at the second end, and the second opening is opposite to the first opening, and
- the four optical fibers extend from the four sensor openings through the third portion of the internal channel, through the point where the first and third portions of the internal channel meet, through the first portion of the internal channel and the bend in the first portion of the internal channel, through a point where the first and second portions of the internal channel meet, through the second portion of the internal channel, and exiting the second opening at the second end of the handle.

25. The device of claim 24 wherein a perimeter of the handle is greater than a perimeter of the shaft, and
the shaft comprises at most a single bend from the distal end to the proximal end.

26. The device of claim 24 comprising:
a second axis of the first portion of the internal channel passing through the first portion of the shaft, wherein the second axis is angled with respect to the first axis,
the second portion of the shaft is longer than the first portion of the shaft, and
a third axis of the second portion of the internal channel passing through the handle is coaxial with the second axis.

27. The device of claim 24 wherein the four sensor openings are in a linear arrangement that is transverse to the first axis.

* * * * *